(12) United States Patent
Carter et al.

(10) Patent No.: US 7,678,774 B2
(45) Date of Patent: Mar. 16, 2010

(54) TREATING SEVERE ACUTE RESPIRATORY SYNDROME

(75) Inventors: William A. Carter, Spring City, PA (US); David Strayer, Bryn Mawr, PA (US)

(73) Assignee: Hemispherx Biopharma, Philadelphia, PA (US)

( * ) Notice: Subject to any disclaimer, the term of this patent is extended or adjusted under 35 U.S.C. 154(b) by 315 days.

(21) Appl. No.: 11/698,038

(22) Filed: Jan. 26, 2007

(65) Prior Publication Data

US 2007/0141080 A1 Jun. 21, 2007

Related U.S. Application Data

(62) Division of application No. 10/842,474, filed on May 11, 2004, now abandoned.

(60) Provisional application No. 60/470,893, filed on May 16, 2003, provisional application No. 60/517,882, filed on Nov. 7, 2003.

(51) Int. Cl.
*A61K 31/713* (2006.01)
*A61K 38/21* (2006.01)

(52) U.S. Cl. .................... 514/44 R; 424/85.7

(58) Field of Classification Search ................ None
See application file for complete search history.

(56) References Cited

U.S. PATENT DOCUMENTS

| | | | |
|---|---|---|---|
| 4,024,222 | A | 5/1977 | Ts'o et al. |
| 4,130,641 | A | 12/1978 | Ts'o et al. |
| 4,795,744 | A | 1/1989 | Carter |
| 4,820,696 | A | 4/1989 | Carter |
| 4,945,082 | A | 7/1990 | Carter |
| 4,950,652 | A | 8/1990 | Carter et al. |
| 4,963,532 | A | 10/1990 | Carter |
| 5,063,209 | A | 11/1991 | Carter |
| 5,091,374 | A | 2/1992 | Carter |
| 5,132,292 | A | 7/1992 | Carter |
| 5,593,973 | A | 1/1997 | Carter |
| 5,683,986 | A | 11/1997 | Carter |
| 5,712,257 | A | 1/1998 | Carter |
| 5,906,980 | A | 5/1999 | Carter |
| 6,130,206 | A | 10/2000 | Carter |
| 6,372,218 | B1 | 4/2002 | Cummins |
| 6,509,154 | B1 | 1/2003 | De Paillette |
| 7,339,051 | B2 | 3/2008 | Crooke et al. |
| 2005/0002901 | A1 | 1/2005 | Blatt |
| 2005/0070489 | A1 | 3/2005 | Carter et al. |
| 2005/0100885 | A1 | 5/2005 | Crooke et al. |
| 2005/0137154 | A1 | 6/2005 | Strayer et al. |
| 2006/0024271 | A1 | 2/2006 | Alibek et al. |
| 2006/0035859 | A1 | 2/2006 | Carter et al. |
| 2007/0141080 | A1 | 6/2007 | Strayer et al. |
| 2007/0224219 | A1 | 9/2007 | Carter et al. |
| 2008/0019943 | A1 | 1/2008 | Carter et al. |
| 2009/0004141 | A1 | 1/2009 | Carter et al. |

FOREIGN PATENT DOCUMENTS

| | | | |
|---|---|---|---|
| WO | WO 2004/092383 | * | 10/2004 |
| WO | 2005/009337 | | 2/2005 |
| WO | WO 2005/019410 | * | 3/2005 |
| WO | 2006/082435 | | 8/2006 |

OTHER PUBLICATIONS

Barnard et al (Antiviral Chemistry & Chemotherapy 17:275-284, 2006).*
Subbarao et al (Trends in Microbiology 14:299-303, 2006).*
Business Wire "Ampligen® enhances the effectiveness of Tamiflu against avian influenza: Second independent preclinical study confirms dsRNA increases flu vaccine effectiveness" two pages (Sep. 2005).
Business Wire "Hemispherx Biopharma expands evaluation of Alferon N against avian flu, promising effects in bird populations to be expanded based on WHO/UN findings" two pages (Feb. 2005).
Houston Chronicle "Anti-virus drug relieves chronic fatigue syndrome" p. 20 (Oct. 1991).
Ison et al. "Therapeutic options for the management of influenza" Curr. Opin. Pharmcol. 1:482-490 (2001).
Pharma Business Week "Avian influenza, Ampligen enhances the effectiveness of Tamiflu against avian influenza" p. 18 (Oct. 2005).
D'Agostini et al. "Combination Therapy with amantadine and immunomodulators potentiates antiviral effects in influenza a virus-infected mice" Antiviral Res. 20:160 (abstract 217) (1993).
Hayden et al. "Combined interferon-$\alpha_2$, rimantadine hydrochloride, and ribavirin inhibition of influenza virus replication in vitro" Antimicr. Agents and Chemother. 25:53-57 (1984).
Search Report for Singapore Appln. No. 200601533-3 completed May 9, 2007.
Search Report for Singapore Appln. No. 200601533-3 completed Nov. 7, 2007.
World Health Organization, Management of Severe Acute Respiratory Syndrom (SARS), Apr. 11, 2003; http://web.archive.org/web/20030621080706/www.who.int/csr/sars/management/en/print.html.
Zhao et al, Description and clinical treatment of an early outbreak of severe acute respiratory syndrome (SARS) in Guangzhou, PR China. Journal of Medical Microbiology, 2003. vol. 52, pp. 715-720.
Tan et al (Emerging Infectious Diseases 10:581-586, Apr. 2004).
Dahl et al (Scand. J. Infect. Dis. 36: 829-831, 2004).

* cited by examiner

*Primary Examiner*—Mary E Mosher
(74) *Attorney, Agent, or Firm*—Nixon & Vanderhye P.C.

(57) ABSTRACT

Severe acute respiratory syndrome is treated with a natural human alpha interferon, a dsRNA or both natural human alpha interferon and a dsRNA.

12 Claims, No Drawings

TREATING SEVERE ACUTE RESPIRATORY SYNDROME

CROSS REFERENCE TO RELATED APPLICATIONS

This application is a divisional application of Ser. No. 10/842,474 filed May 11, 2004, now abandoned which in turn claims priority from U.S. provisional patent application Ser. No. 60/470,893 filed May 16, 2003 and Ser. No. 60/517,882 flied Nov. 7, 2003.

Procedures are provided for combating the effects of coronavirus-induced conditions by the administration of an α-interferon composed of a mixture of naturally occurring α-interferons or a synthetic, specifically configured, double-stranded ribonucleic acid (dsRNA) or both an α-interferon and a dsRNA.

BACKGROUND

Severe Acute Respiratory Syndrome (SARS) is a new disease that is rapidly spreading within China and other countries around the world. Although, a combination of ribavirin, a synthetic, non-interferon-inducing, broad spectrum antiviral nucleoside, and corticosteroids is commonly used as therapy, especially in China, laboratory testing by the National Institutes of Health (NIH) found ribavirin to have no effect on this coronavirus. This lack of efficacy suggests the need for an effective therapeutic regimen.

DESCRIPTION OF THE INVENTION

Described is use of an α-interferon, preferably a natural, multi-species α-interferon in the treatment of the symptoms associated with SARS in patients including human patients infected with the SARS virus, also referred to as the SARS-associated coronavirus (SARS-CoV). Alternatively, a dsRNA may be used in the treatment of the symptoms associated with SARS-associated coronavirus in patents including human patients infected with the SARS-associated coronavirus. Also described is the coordinated use of both (1) an α-interferon, preferably a natural, multi-species α-interferon and conjointly therewith (2) a dsRNA in the treatment of the symptoms associated with SARS-associated coronavirus in patients including human patients infected the SARS-associated coronavirus. Procedures for attaining a favorable therapeutic and clinical result and compositions for accomplishing the same are described. Preferably the dsRNA is administered with the α-interferon and preferably the dsRNA is $rI_n.r(C_{12}U)_n$, Poly A.Poly U or $rI_n.r(C_{29}G)_n$, in which r is ribo.

In the context of the present invention, what is meant by "coordinated" use is, independently, either (i) co-administration, i.e. substantially simultaneous or sequential administration of the α-interferon and of the dsRNA, or (ii) the administration of a composition comprising the α-interferon and the dsRNA in combination and in a mixture, in addition to optional pharmaceutically acceptable excipients and/or vehicles.

For internal administration the α-interferon may, for example, be formulated in conventional manner for oral or rectal administration. Formulations for oral administration include aqueous solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents.

The α-interferon component of the therapeutic procedures is preferably Alferon N Injection® the only approved natural, multi-species, α-interferon available in the United States. It is the first natural source, multi-species interferon and is a consistent mixture of at least seven species of α-interferon. In contrast, the other available α-interferons are single molecular species of α-interferon made in bacteria using DNA recombinant technology. These single molecular species of α-interferon also lack an important structural carbohydrate component because this glycosylation step is not performed during the bacterial process.

Unlike species of α-interferon produced by recombinant techniques, Alferon N Injection® is produced by human white blood cells which are able to glycosylate the multiple α-interferon species. Reverse Phase HPLC studies show that Alferon N Injection® is a consistent mixture of at least seven species of alpha interferon ($\alpha2, \alpha4, \alpha7, \alpha8, \alpha10, \alpha16, \alpha7$). This natural-source interferon has unique anti-viral properties distinguishing it from genetically engineered interferons. The high purity of Alferon N Injection® and its advantage as a natural mixture of seven interferon species, some of which, like species 8b, have greater antiviral activities than other species, for example, species 2b, which is the only component of Intron A. The superior antiviral activities for example in the treatment of chronic hepatitis C virus (HCV) and (HIV) and tolerability of Alferon N Injection® compared to other available recombinant interferons, such as Intron A and Roferon A, have been reported.

It is reported Alferon N Injection® has activity against a natural coronavirus infection in pigs. Transmissible gastroenteritis (TGE) coronavirus causes an acute gastroenteritis in swine. The diarrhea and dehydration caused by this viral infection result in a high mortality rate in neonates with severity inversely related to the age of the animal. In fact, in piglets less than 14 days of age the morality/morbidity rate typically approaches 100%. Piglets, ages 1-12 days treated with 1.0, 10.0, or 20.0 IU of Alferon N Injection® were found to have an increased survival compared to the control group indicating benefit of this natural mixture of α-interferons in combating this particular coronavirus.

The invention includes methods of enhancing therapy against coronaviruses by administering to patients interferons, particularly natural human alpha interferon and together or conjointly a synthetic, specifically configured, double-stranded ribonucleic acid (dsRNA). The dsRNA of choice is AMPLIGEN® rintatolimod, a synthetic, specifically configured, double-stranded ribonucleic acid (dsRNA) which retains the immunostimulatory and antiviral properties of other double-stranded RNA molecules (dsRNA) but exhibits greatly reduced toxicity. Like other dsRNA, AMPLIGEN® rintatolimod can elicit the induction of interferon and other cytokines. AMPLIGEN® rintatolimod has the ability to stimulate a variety of dsRNA-dependent intracellular antiviral defense mechanisms including the 2',5'-oligoadenylate synthetase/RNase L and protein kinase enzyme pathways.

The mismatched dsRNA may be of the general formula $rI_n.r(C_{12}U)_n$. In this and the other formulae that follow r=ribo. Other mismatched dsRNAs for use in the present invention are based on copolynucleotides selected from poly $(C_m,U)$ and poly $(C_mG)$ in which m is an integer having a value of from 4 to 29 and are mismatched analogs of complexes of polyriboinosinic and polyribocytidilic acids, formed by modifying $rI_n.rC_n$ to incorporate unpaired bases (uracil or guanine) along the polyribocytidylate ($rC_m$) strand. Alternatively, the dsRNA may be derived from r(I).r(C) dsRNA by modifying the ribosyl backbone of polyriboinosinic acid ($rI_n$), e.g., by including 2'-O-methyl ribosyl residues. The mismatched may be complexed with an RNA-stabilizing polymer such as lysine cellulose. Of these mismatched analogs of $rI_n \cdot rC_n$, the preferred ones are of the general formula $rI_n \cdot r(C_{11-14}, U)_n$ or $rI_n \cdot r(C_{29}, G)_n$, and are described by Carter and Ts'o in U.S. Pat. Nos. 4,130,641 and 4,024,222 the disclosures of which are hereby incorporated by reference. The dsRNA's described therein generally are suitable for use according to the present invention.

Other examples of mismatched dsRNA for use in the invention include:

$r(I) \cdot r(C_4, U)$ $r(I) \cdot r(C_7, U)$ $r(I) \cdot r(C_{13}, U)$ $r(I) \cdot r(C_{22}, U)$ $r(I) \cdot r(C_{20}, G)$ and $r(I) \cdot r(C_{p \cdot 23}, G_{>p})$.

Alternatively the dsRNA may be the matched form, thus polyadenylic acid complexed with polyuridylic acid (poly A.poly U) may also be used.

When administered 24 hours prior to viral challenge, ampligen has been demonstrated in viral cytopathic inhibition assays and neutral red assays to inhibit human coronavirus strain OC-43, thus suggesting protective activity of ampligen against human chromavirus prior to an encounter with this virus.

α-interferon and/or the dsRNA may be administered for therapy by any suitable route including oral, rectal, nasal, topical (including transdermal, buccal and sublingual), vaginal and parenteral (including subcutaneous, intramuscular, intravenous intradermal, and intravitreal). It will be appreciated that the preferred route will vary with the condition and age of the recipient, the nature of the infection and the chosen active ingredient.

As indicated above, severe acute respiratory syndrome (SARS) is caused by a newly identified member of the coronavirus family. AMPLIGEN® rintatolimod a double-stranded RNA (dsRNA), is reported to exhibit antiviral activity against the coronavirus, Mouse Hepatitis Virus Type-3 (MHV-3) see Hepatology 3:837, 1983. MHV-3 is a coronavirus which causes both a fulminant and a chronic form of hepatitis depending on the mouse strain studied. AMPLIGEN® rintatolimod treatment had a positive effect against the MHV-3 coronavirus in both mouse models. In an acute infection model, Balb/cJ mice exposed to MHV-3 and then treated twice with AMPLIGEN® rintatolimod survived up to four times longer than untreated mice. Since no treatment was given beyond 24 hours post-exposure, it is likely that additional AMPLIGEN® rintatolimod treatments would have had an even greater impact on survival. In the chronic hepatitis model, C3H mice treated after exposure to the MHV-3 coronavirus cleared the virus quickly and did not develop chronic hepatitis. Thus, AMPLIGEN® rintatolimod has shown activity against the coronavirus, MHV-3, in two different mouse models, increasing survival in the acute infection model and completely abrogating the infection in the chronic model.

In a further study it has been determined Alferon® inhibits SARS-CoV at a high specific activity in Vero 76 cells (African green monkey) in culture. Alferon® is a highly purified natural a-interferon obtained from human leucocytes and consists of seven different α-interferon amino acid sequences α2, α4, α7, α8, α10, α16, and α17). Inhibition was quantitated by visual cytopathic effect (CPE), inhibition of the cellular uptake of the vital dye, neutral red (NR), and by virus yield reduction. NR assay was conducted immediately following visual assay. Fifty-percent effective doses (EC5O) were calculated for both CPE and NR assays by regression analysis. Quantitative values for viral yield reduction assays were expressed as 90% effective concentrations (EC9O), representing the drug concentration required to reduce SARS-CoV titers by one $\log_{10}$ and were calculated by regression analysis. Vein cells infected at a MOI of 0.001 visually exhibited 100% CPE over a 3-5 day incubation period without treatment. Alferon® inhibited SARS-CoV at an ECSO=5,696+/−1,703 (SEM) IU/ml (visual) and 10,740+/−5,161 (SEM) IU/ml (NR). Viral load reduction by one $\log_{10}$ was 78,000+/−22,000 (SEM) IU/ml.

The beneficial effects of Alferon® are also reported by Tan et al, Emerging Infectious Diseases—www.cdc.gov/eid—Vol. 10 No. 4, April 2004, in which several commercially available, clinically approved compounds from several antiviral pharmacologic classes screened to determine the presence of in vitro anti-SARS-CoV activity. Of the 18 antiviral compounds tested Alferon® was found to be the most active FDA-approved interferon when tested against the SARS coronavirus. This contrasts with the recombinant α-interferons, Roferon and Intron A, which were not found to be active against the SARS coronavirus when tested at much higher concentrations.

It is also reported the activity of interferon can potentially be amplified by the addition of a double-stranded RNA drug, AMPLIGEN® rintatolimod. While interferon up-regulates certain intracellular antiviral pathways, dsRNAs, like AMPLIGEN® rintatolimod, are required to fully activate these important antiviral pathways. When interferons are combine with AMPLIGEN® rintatolimod synergistic antiviral and antitumor effects are seen. Moreover, AMPLIGEN® rintatolimod has already shown strong antiviral activity in two separate animal models of the coronavirus (MHV-3). Although uncertainty now exists regarding the characteristics of this coronavirus, in the event it is determined the SARS-associated coronavirus elaborates IFN neutralizing products, AMPLIGEN® rintatolimod has potential to override these inhibitors and achieve an antiviral effect.

In addition, as a further attribute of the dsRNA arm of the disclosed therapeutic combination therapy, synergistic antiviral and antitumor effects have been demonstrated using AMPLIGEN® rintatolimod treatment in combination with all three types of interferon (α, β and γ). These synergistic effects have been seen against HIV and a variety of different histologic tumor types. Four human tumor cell lines were studied for their response to antiproliferative effects of AMPLIGEN® rintatolimod in combination with various interferons. Results indicate that (1) AMPLIGEN® rintatolimod worked synergistically with all interferons in all cell lines studied; (2) growth inhibition of cells resistant to interferons can be potentiated by low doses of AMPLIGEN® rintatolimod; (3) the antiproliferative effect of interferons can be potentiated by AMPLIGEN® rintatolimod in AMPLIGEN® rintatolimod-resistant cells; and (4) AMPLIGEN® rintatolimod works by a mechanism(s) other than, or in addition to, the induction of interferon. See Montefiori, AIDS Res. and Human Retroviruses 5:193-203, 1989 and Hubbell, Int. J. Cancer 37:359-365, 1986.

The recommended dosage of the components will depend on the clinical status of the patient and the experience of the clinician in treating similar infection. As a general guideline dosage of Alferon N Injection® utilized for systemic infections is 5 to 10 million units (sq) thrice weekly. The AMPLIGEN® rintatolimod dose schedule is 400 mg by IV infusion twice weekly, although these amounts and/or dosage frequency may be varied by the clinician in response to the patient's condition. The components may be administered at the same time, for instance as mixture of the α-interferon and dsRNA, independently as the α-interferon then the dsRNA or the α-interferon and the dsRNA may be administered in a time-spaced manner.

EXAMPLE

Effects of Alferon N®, an alfa-n3 human interferon, on the replication of SARSCoV in vitro.

Vero 76 cells (African green monkey kidney) were obtained from American Type Culture Collection (Manassas, Va.). The growth medium was Eagle's minimum essential medium with non-essential amino acids (MEM), 5% FBS and 0.1% $NaHCO_3$. The test medium was MEM supplemented with 2% FBS, 0.18% $NaHCO_3$ and 50 μg gentamicin/ml. The SARS coronavirus, strain 200300592 (Urbani), was obtained from James Comer (Centers for Disease Control, Atlanta, Ga.). Human leukocyte derived interferon alfa-n3 (03-6600) was kindly provided by Hemispherx Biopharma, Inc. (New Brunswick, N.J.) as a stock solution of $5\times10^6$ units/ml.

Using cytopathic effect (CPE) reduction assays read visually and verified spectrophotometrically by neutral red (NR) uptake assay of the same plate (Barnard et al., 2001), an interferon alfa-n3 was evaluated for anti-SARSCoV activity in Vera 76 cells.

Virus at a multiplicity of infection of 0.001 was added to 96 well plates seeded with near confluent monolayers of cells in which drug had been serially diluted, using 10-fold or ½ log dilution series. Addition of virus was within five minutes after exposure of cells to drug.

The cells were incubated at 37° C. until the untreated virus controls displayed destruction of the monolayers (100% CPE, 3-5 days). The plates were then scored for cytotoxicity and viral CPE by microscopic examination, usually followed immediately by neutral red staining and processing for spectrophotometric reading. EC50 values (the concentration of compound needed to inhibit the cytopathic effect to 50% of the control value) and IC50 values (the concentration at which uptake of neutral red or cytotoxic effects was reduced by 50% compared to control cells) was calculated by regression analysis. Values were expressed as mean±the standard error of the mean. For the visual assay, n=10 and for the NR assay, n=5. A selective index (IC50/EC5O) for each compound was then calculated. Compounds found active by these assays were then further evaluated for inhibitory activity in two separate virus yield reduction assays (Barnard et al., 2001). EC9O values were derived by regression analysis from those assays and represent the concentration at which virus yields were reduced by 1 $\log_{10}$. The EC9O values were averaged and the average was expressed as the mean the ± standard error of the mean.

It was found Alferon N® inhibited SARSCoV, with an EC5O=5,696±1703 IU by visual CPE inhibition assay and an EC5O 10,740±5,161 IU/ml by NR assay. However, viral cytopathic effects (CPE) were readily apparent at all dilutions tested, although at higher compound doses, CPE was greatly reduced compared to the virus replication controls (data not shown). This phenomenon was verified by virus yield reduction assay in which each dilution of drug was sampled and quantified for the presence of surviving virus or newly produced virus. At each dilution of compound, infectious virus was detected, with lower amounts of virus being detected at the higher concentrations of compound (data not shown). The concentration at which virus load was reduced by 1 log 10 (EC9O) 78 000±22,000 IU/ml.

From these studies it was determined Alferon N® worked well in reducing virus cytopathic effect, with an EC5O of 5,696±1703 IU/ml.

Cinatl J, Morgenstern B, Bauer G, Chandra P, Rabenau H, Doerr H W. Treatment of SARS with human interferons. *Lancet* 2003; 362:293-4.

Barnard D L, Stowell V D, Seley K L, Hegde V R, Das S R, Rajappan V P, et al. Inhibition of measles virus replication by 5'-nor carbocyclic adenosine analogues. *Antiviral Chem Chemother* 2001; 12:241-250.

What is claimed is:

1. A method of treating severe acute respiratory syndrome comprising administering to an infected subject a dsRNA; wherein the dsRNA is $rI_n.r(C_{11-14},U)_n$, Poly A.Poly U, or $rI_n.r(C_{29},G)_n$ in which n is an integer and r is ribo.

2. A method of treating severe acute respiratory syndrome comprising the coordinated administration to an infected subject of (1) a natural human alpha interferon and (2) a dsRNA: wherein the dsRNA is $rI_n.r(C_{11-14},U)_n$, Poly A.Poly U, or $rI.r(C_{29},G)_n$ in which n is an integer and r is ribo.

3. The method according to claim 1, wherein the dsRNA is $rI_n.r(C_{12}U)_n$.

4. The method according to claim 2, wherein the dsRNA is $rI_n.r(C_{12}U)_n$.

5. The method according to claim 2, wherein the interferon is administered orally.

6. The method according to claim 2, wherein the interferon is administered intravenously.

7. The method according to claim 2, wherein the interferon is administered intramuscularly.

8. The method according to claim 2, wherein the interferon is administered subcutaneously.

9. The method according to claim 4, wherein the interferon is administered orally.

10. The method according to claim 4, wherein the interferon is administered intravenously.

11. The method according to claim 4, wherein the interferon is administered intramuscularly.

12. The method according to claim 4, wherein the interferon is administered subcutaneously.

* * * * *